(12) United States Patent
Mostapha et al.

(10) Patent No.: US 11,585,876 B2
(45) Date of Patent: Feb. 21, 2023

(54) SYSTEM AND METHOD FOR MRI COIL SENSITIVITY ESTIMATION AND RECONSTRUCTION

(71) Applicant: Siemens Healthcare GmbH, Erlangen (DE)

(72) Inventors: Mahmoud Mostapha, Princeton, NJ (US); Boris Mailhe, Plainsboro, NJ (US); Mariappan S. Nadar, Plainsboro, NJ (US); Simon Arberet, Princeton, NJ (US); Marcel Dominik Nickel, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/577,148

(22) Filed: Jan. 17, 2022

(65) Prior Publication Data

US 2022/0252683 A1    Aug. 11, 2022

(30) Foreign Application Priority Data

Feb. 5, 2021    (EP) .................................... 21155573

(51) Int. Cl.
*G01R 33/24*    (2006.01)
*G01R 33/56*    (2006.01)
*G01R 33/561*   (2006.01)
*G16H 30/20*    (2018.01)

(52) U.S. Cl.
CPC ....... *G01R 33/246* (2013.01); *G01R 33/5608* (2013.01); *G01R 33/5611* (2013.01); *G16H 30/20* (2018.01)

(58) Field of Classification Search
CPC .............. G01R 33/246; G01R 33/5608; G01R 33/5611
See application file for complete search history.

(56) References Cited

U.S. PATENT DOCUMENTS

| 10,302,713 | B2 * | 5/2019 | Popescu ............. G01R 33/5611 |
| 10,712,416 | B1 * | 7/2020 | Sandino ................ G06T 11/008 |
| 2018/0120402 | A1 * | 5/2018 | Nehrke ................ G01R 33/243 |
| 2020/0294282 | A1 | 9/2020 | Schlemper et al. |
| 2020/0300954 | A1 | 9/2020 | Sharma |

OTHER PUBLICATIONS

Anatole Moreau et al.: "Deep transformnetworks for scalable learning of MRreconstruction", Proceedings of the International Societyfor Magnetic Resonance in Medicine, ISMRM,27th Annual Meeting and Exhibition,Montreal, Quebec, Canada, May 11-16, 2019,No. 4778, Apr. 26, 2019.

(Continued)

*Primary Examiner* — Gregory H Curran

(57) ABSTRACT

A system is provided for MRI coil sensitivity estimation and reconstruction At least two cascades of regularization networks are serially connected such that the output of a cascade is used as input of a following cascade, at least two deepsets coil sensitivity map networks are serially connected such that the output of a deepsets coil sensitivity map network is used as input of a following deepsets coil sensitivity map network (CR), and wherein the outputs of the deepsets coil sensitivity map networks are also used as inputs for the cascades.

18 Claims, 8 Drawing Sheets

(56) References Cited

OTHER PUBLICATIONS

European Search Report for European Application No. 21155573.5-1126 dated Jul. 7, 2021.
Matthew J Muckley et al:"State-of-the-art Machine Learning MRIReconstruction in 2020: Results of theSecond fastMRI Challenge", arxiv.org, Cornell University Library, 201OLin Library Cornell University Thaca, NY14853, Dec. 9, 2020.
Uecker, Martin, et al. "ESPIRiT—an eigenvalue approach to autocalibrating parallel MRI: where SENSE meets GRAPPA." Magnetic resonance in medicine 71.3 (2014): 990-1001.
Zaheer, Manzil et al: "Deep Sets"; arxiv.org; Cornell University Library; XP081311878.
U.S. Appl. No. 17/484,017, filed Sep. 24, 2021.

* cited by examiner

SYSTEM AND METHOD FOR MRI COIL SENSITIVITY ESTIMATION AND RECONSTRUCTION

RELATED APPLICATION

This application claims the benefit of EP 21155573.5, filed Feb. 5, 2021, which is hereby incorporated by reference in its entirety.

FIELD

The present embodiments describe a system and a method for magnetic resonance imaging (MRI) coil sensitivity estimation and reconstruction and especially for controlling a magnetic resonance imaging system (MRI system). Especially, the embodiments describe coil sensitivity estimation with deep-sets towards end-to-end accelerated MRI reconstruction.

BACKGROUND

Parallel imaging (PI) is a crucial technique for accelerating data acquisition in magnetic resonance imaging (MRI), which is exceedingly time-consuming. In parallel imaging, multiple receiver coils are utilized to simultaneously acquire various views of the underlying anatomy, which are then optimally combined. Each coil induces a sensitivity map ("coil sensitivity map": CSM) that is multiplied pointwise with the corresponding coil image for optimal Signal-to-Noise Ratio (SNR) reconstruction. Such coil sensitivity maps are typically estimated using the fully sampled central region of k-space corresponding to low frequencies, called the Auto-Calibration Signal (ACS).

However, since parallel Imaging is generally combined with Compressed Sensing (CS) methods for further acceleration of MRI acquisition, it is desirable to have a CSM estimation approach that can operate on subsampled auto-calibration signals and that can also be combined with current deep learning reconstruction models in an end-to-end learning framework for optimal results. Therefore, there is the need for an effective deep learning network that can estimate CSMs accurately from fully or subsampled ACS, which needs to be permutation invariant or equivariant to handle a varying number of coils without any explicit ordering typically encountered in practical settings.

The eigenvalue approach to autocalibrating parallel MRI ("ESPIRiT") applies an eigendecomposition of the reconstruction operator for each coil's pixel location in the image domain to obtain the required CSMs. Such an approach has several limitations, which include computational complexity (it is time-consuming), especially for more significant imaging problems (e.g., 3D problems). Moreover, to accurately estimate these sensitivity maps, the ACS must be sufficiently large, which limits the maximum possible acceleration, particularly for dynamic MRI. Additionally, such an approach can only be applied to fully sampled ACS, limiting further acceleration using CS methods for the central region of k-space corresponding to low frequencies. Finally, such a CSM estimation approach can't be combined with MRI deep learning reconstruction models in an end-to-end learning framework, restricting the overall performance and accuracy of the system.

SUMMARY

It is the object to improve the known systems, devices, and methods to facilitate an improvement in MRI coil sensitivity estimation and reconstruction and especially in controlling a magnetic resonance imaging system.

This object is achieved by a system, a method, a control device, and a magnetic resonance imaging system.

A system for MRI coil sensitivity estimation and reconstruction according to one embodiment includes the following components:

at least two cascades of regularization networks that are serially connected such that the output of a cascade is used as input of a following cascade, at least two deepsets coil sensitivity map networks that are serially connected such that the output of a deepsets coil sensitivity map network is used as input of a following deepsets coil sensitivity map network, wherein the outputs of the deepsets coil sensitivity map networks are also used as inputs for the cascades.

Cascades of regularization networks and coils sensitivity map networks CSM are well known in the art. However, deepsets coil sensitivity map networks are not commonly used for such approach.

This architecture results in a trainable MRI reconstruction system formulated as a trainable unrolled optimization framework with several cascades of regularization networks and varying data consistency layers. The CSM networks (coil sensitivity map networks) should be present at each cascade to present an optimal solution.

As explained in the following, the CSM networks should be deepsets coil sensitivity map estimation and refinement networks (DS-CSME and DS-CSMR in short), enabling an integrated deep learning solution that enables end-to-end training for allowing for further MRI acceleration while preserving the overall reconstructed image quality. In particular, the first CSM network should be a DS-CSME to estimate CSM from an auto-calibration signal ACS, while the following CSM networks should be DS-CSMR used to refine the estimated CSM after each reconstruction cascade if its usage was enabled.

The acquired data of the coils is inputted from the data acquisition into the first cascade and the deepsets coil sensitivity map (especially estimation) network. Then, the data is further processed by the following cascades and deepsets coil sensitivity map (preferably refinement) networks. It is preferred to share the weights of the CSMs (especially of DS-CSMRs) among the reconstruction cascades.

The CSM estimation problem is naturally expressed as operating on sets of entities rather than vectors. The size X of the set (i.e., the number of coils) is not fixed in advance, and there is no inherent ordering to entities (coils k-space data) in the set. Therefore, the proposed DS-CSME is restricted to a permutation invariant or equivariant functions (i.e., deepsets), which has a particular structure and can be decomposed for suitable transformations $\rho$ and $\varphi$ for a coil x in the form of:

$$\rho\left(\sum_{x \in X} \varphi(x)\right).$$

A method for training a system according to one embodiment includes the following acts:

providing a plurality of training datasets, each training dataset including multi-coil MRI-imaging data, especially under-sampled multi-coil k-space data, and a ground truth including a fully-sampled multi-coil k-space data (of this MRI-imaging data), training of the system with the training datasets concerning the ground truth of each training dataset. Although typically no labelled ground truth images are necessary, they can be used to pre-train the CSM estimation and refinement models.

A control device (controller) according to one embodiment for controlling a magnetic resonance imaging system includes the system. Alternatively, or additionally, the control device is designed to perform the method. The control device may include additional units or devices for controlling components of a magnetic resonance imaging system, e.g., a sequence control unit for measurement sequence control, a memory, a radio-frequency transmission device that generates, amplifies and transmits RF pulses, a gradient system interface, a radio-frequency reception device to acquire magnetic resonance signals, and/or a reconstruction unit (processor) to reconstruct magnetic resonance image data.

A magnetic resonance imaging system according to one embodiment includes the control device.

Some units or modules of the system or the control device mentioned above can be completely or partially realized as software modules running on a processor of a system or a control device. A realization largely in the form of software modules can have the advantage that applications already installed on an existing system can be updated, with relatively little effort, to install and run these units of the present application. The object is also achieved by a computer program product with a computer program that is directly loadable into the memory of a device of a system or a control device of a magnetic resonance imaging system, and which includes program units to perform the acts of the inventive method when the program is executed by the control device or the system. In addition to the computer program, such a computer program product can also include further parts such as documentation and/or additional components, also hardware components such as a hardware key (dongle etc.) to facilitate access to the software.

A non-transitory computer readable medium such as a memory stick, a hard-disk or other transportable or permanently-installed carrier can serve to transport and/or to store the executable parts (instructions) of the computer program product so that these can be read and executed by a processor unit (processor) of a control device or a system. A processor unit can include one or more microprocessors or their equivalents.

Particularly advantageous embodiments and features are given by the dependent claims, as revealed in the following description. Features of different claim categories (e.g., system, method, . . . ) may be combined as appropriate to give further embodiments not described herein.

Preferably, the first deepsets coil sensitivity map network of the serial connection is a deepsets coil sensitivity map estimation network (DS-CSME) and the following deepsets coil sensitivity map networks are deepsets coil sensitivity map refinement networks (DS-CSMR). Preferably, deepsets coil sensitivity map estimation and refinement networks are used, to enable an integrated deep learning solution that enables end-to-end training for allowing for further MRI acceleration while preserving the overall reconstructed image quality. In particular, the proposed deepsets coil sensitivity map estimation network (DS-CSME) is used first to estimate CSM from the auto-calibration signal (ACS), while the proposed deepsets coil sensitivity map refinement network (DS-CSMR) is used to refine the estimated CSM after each reconstruction cascade if its usage was enabled.

If a CSM is the input, there is no need for a DS-CSME at the beginning. However, in general it is advantageous to estimate the CSM at the start.

Preferably, the number of deepsets coil sensitivity map networks is equal to the number of cascades and preferably each cascade is connected to an output of an individual deepsets coil sensitivity map network according to the serial arrangement of cascades and deepsets coil sensitivity map networks. This means that the output of the first CSM network is connected to the first cascade, the output of the second CSM network is connected to the second cascade and so on. The system should be a trainable unrolled optimization framework with several cascades of regularization networks and varying data consistency layers. Thus, it is advantageous to have CSM networks at each cascade.

Preferably, the outputs of a number of the deepsets coil sensitivity map networks are weighted using shared weights, preferably wherein all deepsets coil sensitivity map networks are weighted that are deepsets coil sensitivity map refinement networks. It is, thus, preferred to share the weights of the CSM networks (i.e., especially the DS-CSMR) among the reconstruction cascades.

It is preferred that in the system described above, a special architecture of a deepsets coil sensitivity map network DS-CSME and/or DS-CSMR is used.

A preferred deepsets coil sensitivity map network includes a number of input channels each with a number of two or more successive deep iterative hierarchical networks ("DIHN"). Preferably, each channel has the same number of DIHN, and the DIHN of the channels are united in form of a number of successive deep-sets-blocks, wherein each deep-sets-block includes a DIHN for each channel, preferably followed by a RSS-normalization.

A preferred deepsets coil sensitivity map estimation network includes at the entrance of each channel a masking operator that zeros out all lines in k-space except for ACS lines, which is followed by an inverse Fourier transform to compute corresponding coil images.

A preferred deepsets coil sensitivity map refinement network does neither include such masking operator nor such inverse Fourier transform. However, these features may be included even in a DS-CSMR, when needed.

A preferred architecture of a deepsets coil sensitivity map estimation network (DS-CSME), the center k-space for each coil data is first extracted using said masking operator that zeros out all lines except for the ACS lines, which is followed by said inverse Fourier transform (IFT) to compute the corresponding coil images. The input set of coil images is then passed through the deepsets blocks. Each deepset block is preferably composed of said Deep Iterative Hierarchical Network (DIHN see also the following special description) applied for each coil image independently followed by a normalization of the estimated outputs using the root sum square (RSS) to ensure appropriate estimated CSMs.

Regarding the root sum square, a normalization factor NF can be calculated by:

$$NF=\sqrt{(DIHN_i(coil_1))^2+\ldots+(DIHN_i(coil_N))^2}.$$

The normalization factor NF is then used to normalize each CSM separately resulting in N outputs, wherein DIHN #i of coil #j is set to DIHN #i of coil #j/NF.

It should be noted that the computed RSS can also be concatenated to the normalized outputs before applying the next deepsets block.

A preferred architecture of a deepsets coil sensitivity map refinement network (DS-CSMR) has a similar architecture to the preferred DS-CSME, but without the ACS masking and IFT operations.

It is preferred that in the deepsets coil sensitivity map networks DS-CSME and/or DS-CSMR described above, a special architecture of a deep iterative hierarchical network "DIHN" is used.

It is preferred that at least one of the DIHN has an architecture including a feature extraction block followed by two or more successive stages each including a hierarchical U-block and a shared memory block. The data processed by a hierarchical U-block is sent to the memory block of this stage and the hierarchical U-block of the next stage, wherein the outputs of the memory blocks are weighted with shared weights and concatenated.

The general architecture and function of a feature extraction block is known in the art. Its function is to extract N feature maps from an input image (of a defined dimension H×W) and using an x×y convolution (often a 3×3 convolution) on the input image with a stride of z (often 2), which results in N feature maps of size H/z×W/z.

For a "hierarchical U-block", a "normal" U-net could be used that is well known in the art. However, this block is designated here as "hierarchical U-block", since preferably a special hierarchical architecture is used that is based on "normal" U-nets and uses a number of these U-nets in form of a special hierarchy (explained in the following). Thus, the expression "hierarchical U-block" should be read as "normal" U-net, preferably a number of U-nets used in a special setup.

The "memory blocks" (that could also be designated as "shared memory blocks") are known in the art. A preferred setup is a-U-block (i.e., a U-net) without up- or down-sampling. However, there are also other architectures possible.

It is preferred that the concatenated data is processed by a final enhancement stage, by a 1×1 convolution followed by up-scaling using sub-pixel convolution.

A shared memory block that is preferably similar in construction to a U-block but without the down-sampling and up-sampling operations is used to process the extracted feature maps at different levels and to combine the outputs of the hierarchical U-blocks. The memory block outputs are concatenated before passing them to an output or the final enhancement block.

Regarding the input of this DIHN, typically complex images are inputted into the first DIHNs of the architecture of a DS-CSME (the complex images are created by the inverse Fourier transformation). The following DIHNs usually get a CSM as input.

The preferred DIHN is designed to ensure the system is fast and memory-efficient while also robust to variations in MRI intensities and contrasts (e.g., using different scanned organs, acquisition parameters, image resolutions, etc.). As already said above, the input (e.g., a complex image or a CSM) is first passed through an initial feature extraction block where preferably twice the input feature maps are extracted with half the image resolution achieved through convolutions with stride 2.

The extracted features are then passed through the hierarchical U-blocks (explained in the following) that down-sample the input feature maps, allowing efficient processing at a coarser scale before up-sampling the processed feature maps using subpixel convolutions.

To combine the outputs of the hierarchical U-blocks, the shared memory blocks are used to process the extracted feature maps at different levels, then concatenating the memory block outputs before passing them to the final enhancement block.

According to a preferred embodiment, of a DIHN, at least one of the hierarchical U-blocks is a U-block, being a U-net or a series of such U-blocks.

However, it is also preferred that in the DIHN described above, a special architecture of a "hierarchical U-blocks" is used.

Preferably, at least one of the hierarchical U-blocks has a U-net architecture using U-blocks, each being a U-net, with a contracting path and an expansive path, wherein the contracting path is a convolutional network that includes a repeated application of a U-block followed by a convolution and the expansive path includes up-convolutions and U-blocks.

It is preferred that the contracting path includes a U-block followed by a 3×3 convolution, especially with the stride of 2.

Alternatively, or additionally, it is preferred that the expansive path includes a sub-pixel-convolution, especially with a scale of 2 followed by a U-block, especially wherein a 1×1 convolution is used between the sub-pixel-convolution and the U-block.

Particularly preferably, between the contracting path and an expansive path, the data of the contracting path is further processed by an additional U-block.

Preferably, the contracting path has an architecture using a series of a U-block followed by a 3×3 convolution with the stride of 2. It is also preferred that the expansive path begins with a sub-pixel-convolution with a scale of 2.

The hierarchical U-block down-samples the input feature maps by convolutions, allowing efficient processing at a coarser scale before up-sampling the processed feature maps using subpixel convolutions.

Preferably, a hierarchical U-block and/or a U-block has more than two layers, especially three layers.

It is preferred that in the "hierarchical U-blocks" described above, a special architecture of a "U-block" is used. Thus, preferably at least one of the U-blocks has a U-net architecture with a contracting path and an expansive path, wherein the contracting path is a convolutional network that includes a repeated application of convolutions, each followed by a rectified linear unit (ReLU) and a max pooling operation and the expansive path includes up-convolutions.

It is preferred that the contracting path includes: (a) a functional block including a convolution, especially a 3×3 convolution, a group normalization and a rectified linear unit, and (b) a functional block including a convolution, especially a 3×3 convolution, with the stride of 2.

Alternatively, or additionally, it is preferred that the expansive path includes a sub-pixel-convolution, especially with a scale of 2.

In a preferred architecture of a U-block used in the architecture of the hierarchical U-block, in the contracting path there are used two sub-blocks. The first sub-block includes a 3×3 convolution, a group normalization and a function PReLu, each a well-known procedure in the art. The second sub-block indicates a 3×3 convolution with the stride of 2, also a well-known procedure in the art. These two sub-blocks are preferably arranged such that the input is first processed by the first sub-block, after that the result is preferably added with the input by an addition module well known in the art. This is followed by the second sub-block and the result is given to the next layer.

The expansive path also includes the first sub-block, especially with the above-described addition. In the lower layers, this is preferably followed by a 1×1 convolution. Last, in the lower layers, the result of the preceding sub-blocks is preferably inputted in a sub-pixel convolution with the scale of 2.

It is preferred that at the end of the expansive path, the result is again inputted in a series of a number (one, two or more) of first sub-blocks, especially with the above-described addition.

A concatenation is performed as known in the art of U-nets.

In a preferred system according to one embodiment, components of the system are part of a data-network, wherein preferably the data-network and a medical imaging system (i.e., the magnetic resonance imaging system which provides image data) are in data-communication with each other, wherein the data-network preferably includes parts of the internet and/or a cloud-based computing system, wherein preferably the system according to one embodiment or a number of components of this system is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing." In the technical field of "cloud computing," an IT infrastructure is provided over a data-network, e.g., a storage space or processing power and/or application software. The communication between the user and the "cloud" is achieved by data interfaces and/or data transmission protocols.

In the context of "cloud computing," in a preferred embodiment of the method according to one embodiment, provision of data via a data channel (for example a data-network) to a "cloud" takes place. This "cloud" includes a (remote) computing system, e.g., a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system according to one embodiment, the abovementioned units are present on the "cloud" side. A preferred system further includes, a local computing unit (computer) connected to the system via a data channel (e.g., a data-network, particularly configured as RIS or PACS). The local computing unit includes at least one data receiving interface to receive data. Moreover, it is preferred if the local computer additionally has a transmission interface in order to send data to the system.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION OF THE PREFERRED EMBODIMENTS

Figure 1:
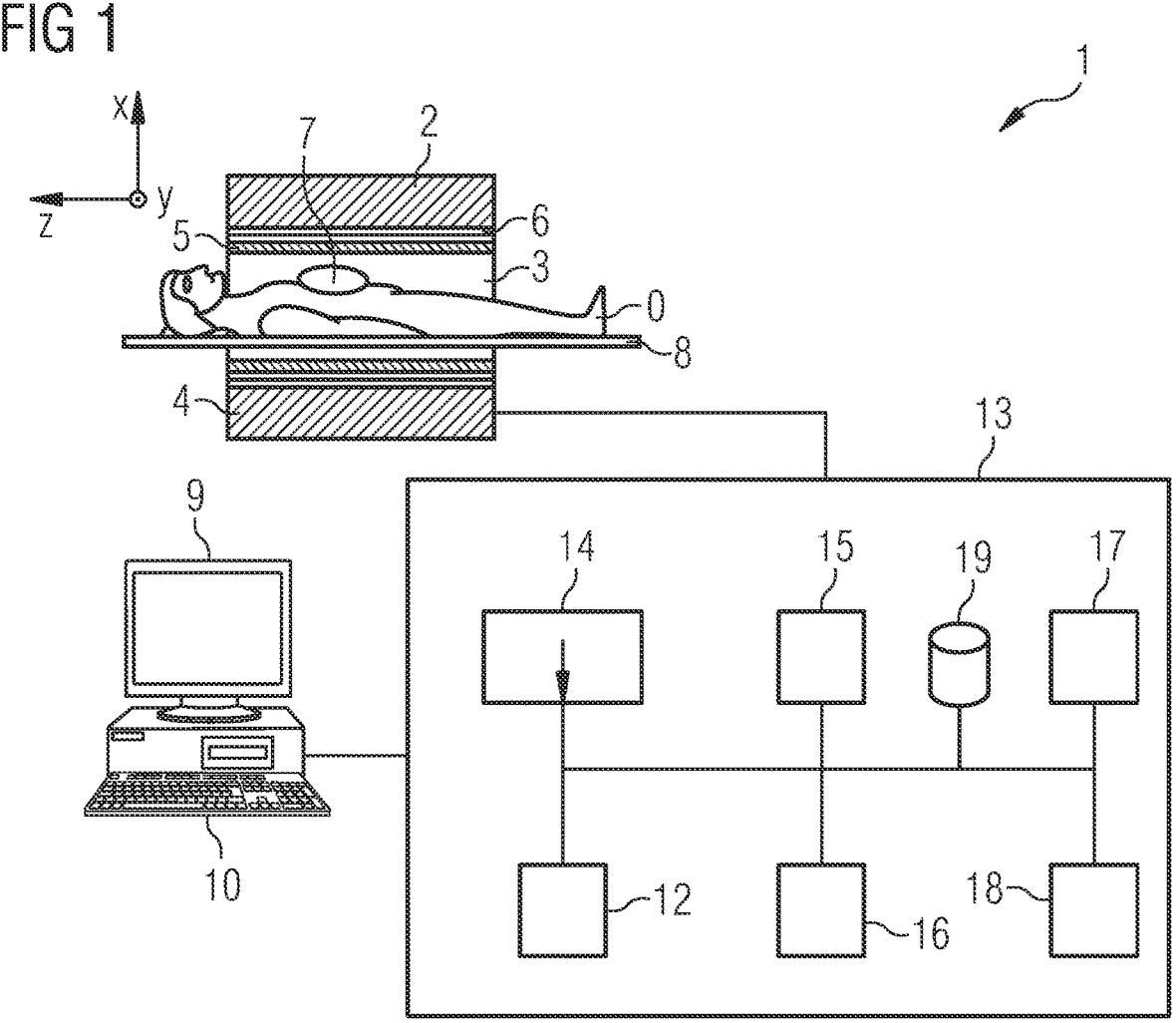
FIG. 1 shows a simplified MRI system with a system according to an embodiment.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person is positioned on a driven bed 8.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as multiple local coils for parallel imaging (symbolized here by only a single local coil) to be arranged on the patient or test subject.

The basic field magnet system 4 is designed in a typical manner so that it generates a basic magnetic field in the longitudinal direction of the patient, i.e., along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the embodiments can also be used at other MRI systems, for example with a laterally open, C-shaped housing, as well as in smaller magnetic resonance scanners in which only one body part can be positioned.

Furthermore, the MRI system 1 has a central control device (controller) 13 that is used to control the MRI system 1. This central control device 13 includes a sequence control unit (sequencer) 14 for measurement sequence control. With this sequence control unit 14, the series of radio-frequency pulses (RF pulses) and gradient pulses can be controlled depending on a selected pulse sequence or, respectively, a series of multiple pulse sequence to acquire magnetic resonance images of the patient O within a measurement session. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device (transmitter) 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device (receiver) 17 (likewise communicating with the sequence control unit 14 in a suitable manner) in order to acquire magnetic resonance signals (i.e., raw data) for the individual measurements, which magnetic resonance signals are received in a coordinated manner from the RF reception antenna system 7 within the scope of the pulse sequence.

A reconstruction unit (processor) 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started by the input unit (possibly in combination with the display unit 9), and in particular suitable control protocols can be selected (and possibly modified) with suitable series of pulse sequence as explained above.

The control device 13 includes a system (computer or processor) 12 designed to perform the method according to an embodiment. A preferred architecture of this system 12 is shown in the following figures. Its components preferably appear to be software modules.

The MRI system 1 according to one embodiment, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
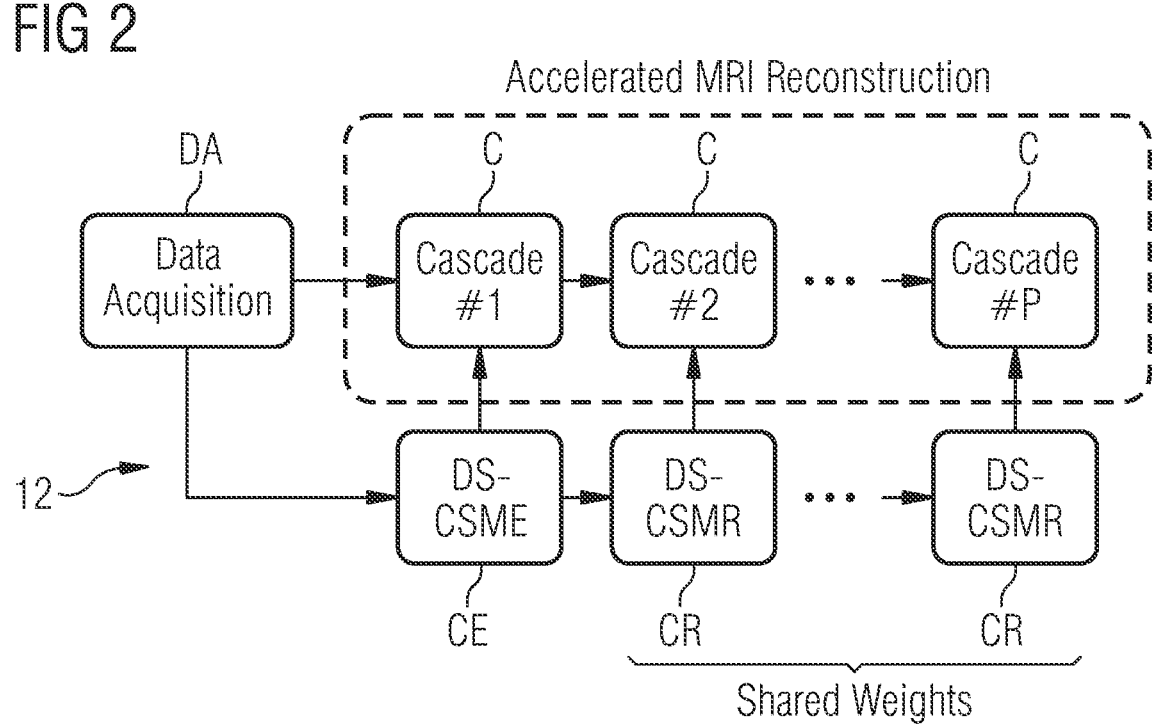
FIG. 2 shows a preferred architecture of a system according to an embodiment.

FIG. 2 shows a preferred architecture of a system according to an embodiment. This architecture uses a deepsets coil sensitivity map estimation network CE (DS-CSME) and several deepsets coil sensitivity map refinement networks CR (DS-CSMR) that are explained in the following.

The system is a trainable unrolled optimization framework with several cascades C of regularization networks and varying data consistency layers, CSMs are needed at each cascade C. Therefore, as shown in this figure, deepsets coil sensitivity map estimation and refinement networks CE, CR (DS-CSME and DS-CSMR in short) are used, enabling an integrated deep learning solution that enables end-to-end training for allowing for further MRI acceleration while preserving the overall reconstructed image quality. In particular, the proposed deepsets coil sensitivity map estimation network CE (DS-CSME) is used first to estimate CSM from the auto-calibration signal (ACS), while the proposed deepsets coil sensitivity map refinement network CR (DS-CSMR) is used to refine the estimated CSM after each reconstruction cascade if its usage was enabled.

The acquired data of the coils is inputted from the data acquisition DA into the first cascade and the deepsets coil sensitivity map estimation network CE (DS-CSME). Then the data is further processed by the following cascades C and deepsets coil sensitivity map refinement networks CR (DS-CSMR). The weights the DS-CSMR CR is shared among the reconstruction cascades.

The CSM estimation problem is naturally expressed as operating on sets of entities rather than vectors. The size X of the set (i.e., the number of coils) is not fixed in advance, and there is no inherent ordering to entities (coils k-space data) in the set. Therefore, the proposed DS-CSME CE is restricted to a permutation invariant or equivariant functions (i.e., deepsets), which has a particular structure and can be decomposed for suitable transformations $\rho$ and $\varphi$ for a coil x in the form of:

$$\rho\left(\sum_{x \in X} \varphi(x)\right).$$

Figure 3:
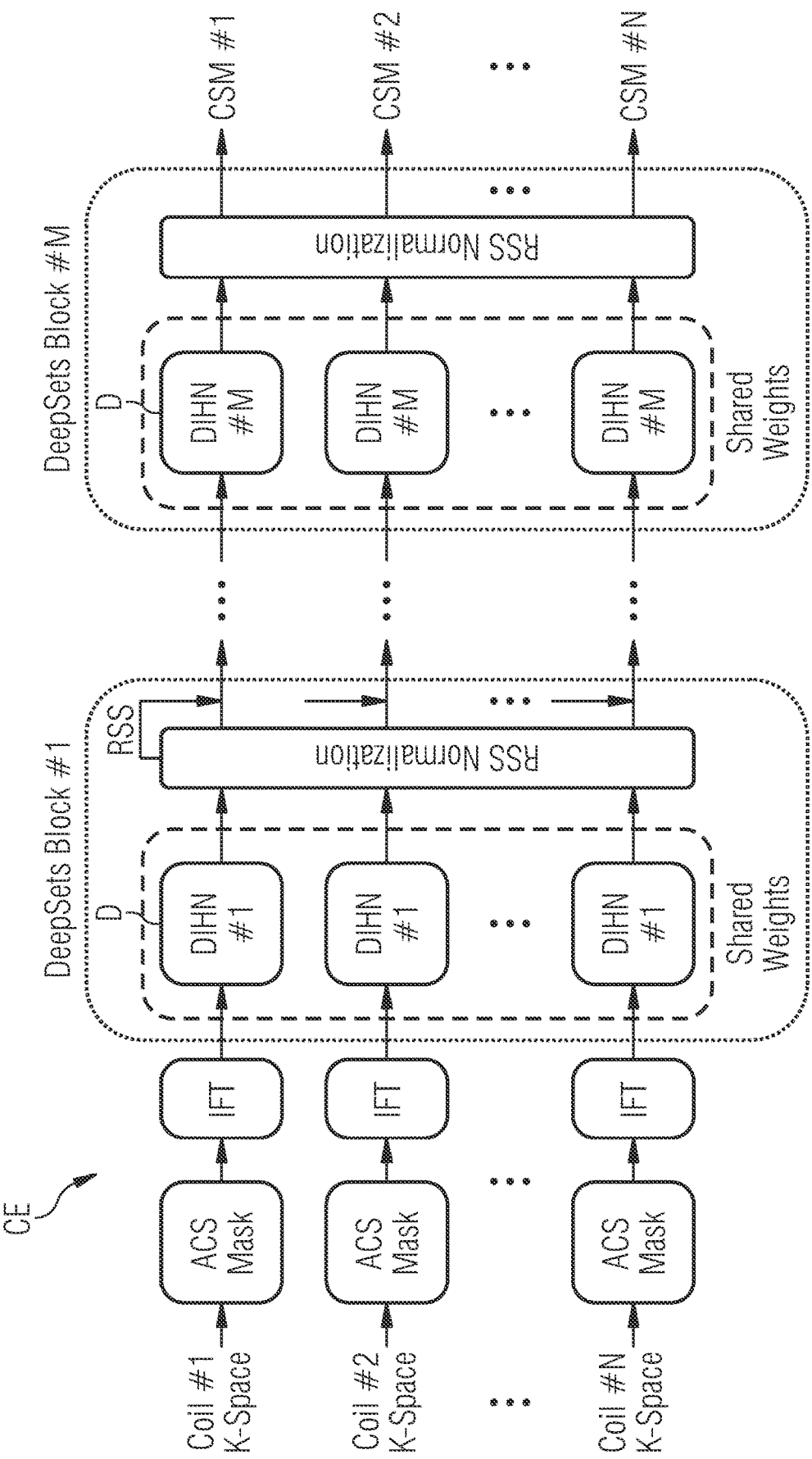
FIG. 3 shows one embodiment of a preferred architecture of a DS-CSME.

FIG. 3 shows a preferred architecture of a deepsets coil sensitivity map estimation network CE (the DS-CSME "block" in FIG. 2). In the proposed DS-CSME CE, the center k-space for each coil data is first extracted using a masking operator that zeros out all lines except for the ACS lines, which is followed by an inverse Fourier transform (IFT) to compute the corresponding coil images. The input set of coil images is then passed through deepsets blocks. Each deepset block is in this example composed of a novel Deep Iterative Hierarchical Network D (DIHN, explained in the following) applied for each coil image independently followed by a normalization of the estimated outputs using the root sum square (RSS) to ensure appropriate estimated CSMs.

Regarding the root sum square, a normalization factor NF can be calculated by:

$$NF = \sqrt{(DIHN_i(coil_1))^2 + ... + (DIHN_i(coil_N))^2}.$$

The normalization factor NF is then used to normalize each CSM separately resulting in N outputs, wherein DIHN #i of coil #j is set to DIHN #i of coil #j/NF.

It should be noted that the computed RSS can also be concatenated to the normalized outputs before applying the next deepsets block.

Figure 4:
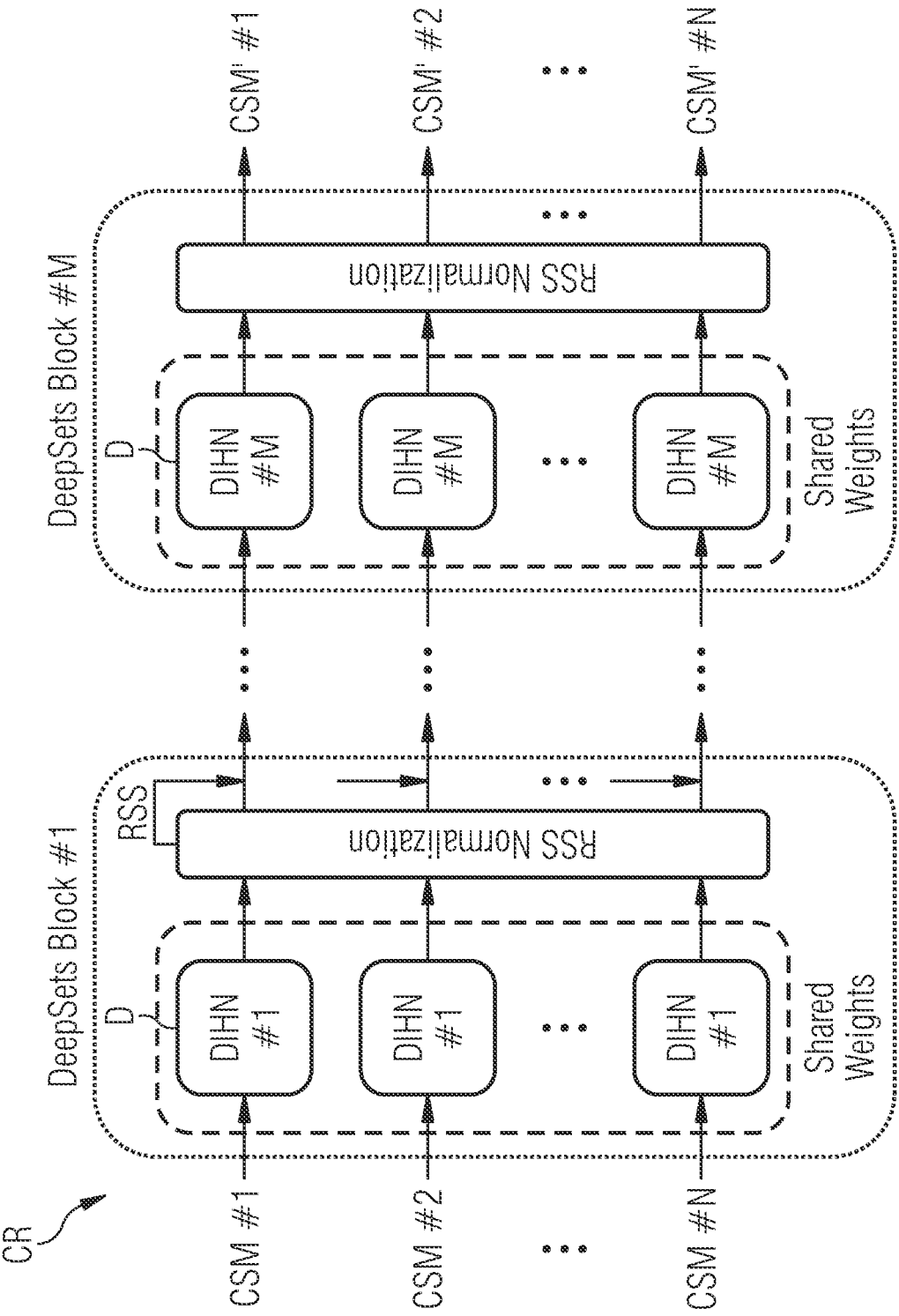
FIG. 4 shows one embodiment of a preferred architecture of a DS-CSMR.

FIG. 4 shows a preferred architecture of a deepsets coil sensitivity map refinement network CR (the DS-CSMR "blocks" in FIG. 2). Applied to the initially estimated CSMs, the proposed DS-CSMRs CR have a similar architecture to the proposed DS-CSME CE of FIG. 3, but without the ACS masking and IFT operations.

As a preferred embodiment, an image-to-image translation network is proposed, referred to as "Deep Iterative Hierarchical Network" (DIHN), with a hierarchical design that iteratively down-samples the input image feature maps followed by an up-sampling procedure, which is used as the primary building block of the proposed deepsets block.

Figure 5:
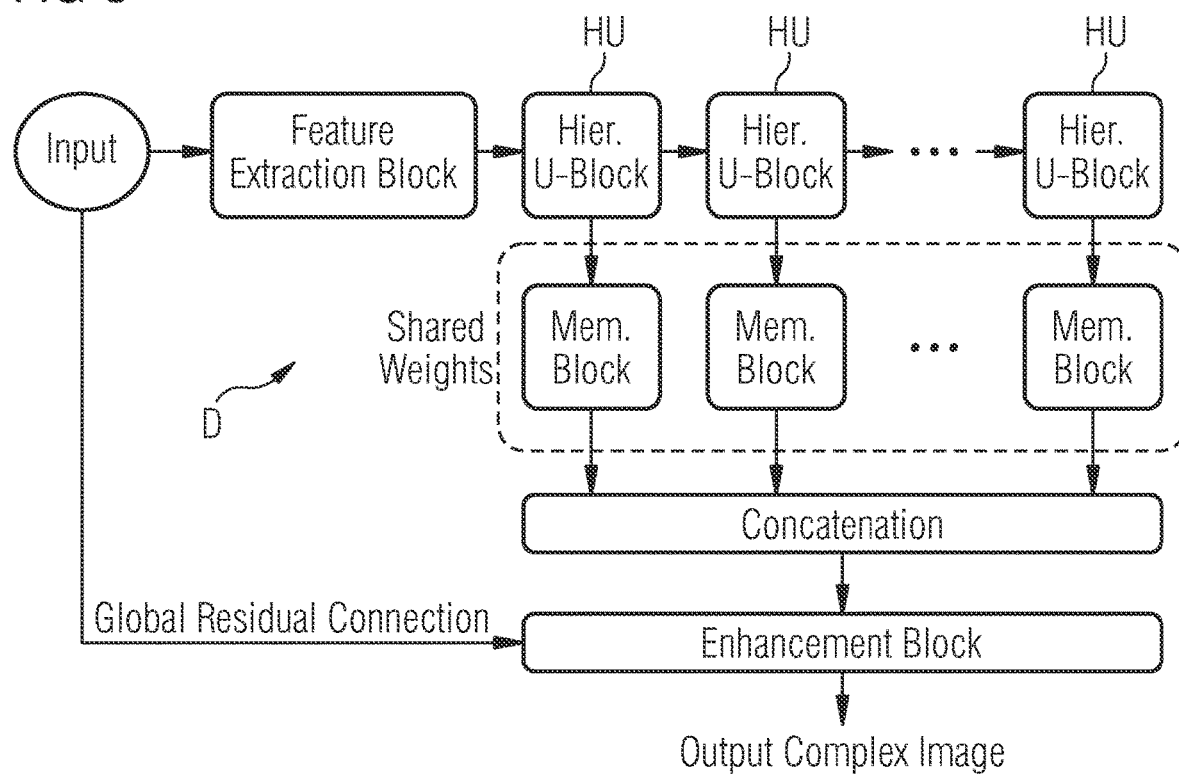
FIG. 5 shows one embodiment of a preferred architecture of a DIHN.

FIG. 5 shows a preferred architecture of a deep iterative hierarchical network D (the DIHN "blocks" of FIGS. 3 and 4).

The proposed DIHN D is designed to ensure the system being fast and memory-efficient while also robust to variations in MRI intensities and contrasts (e.g., using different scanned organs, acquisition parameters, image resolutions, etc.). As shown in this figure, the input (e.g., a complex image or a CSM) is first passed through an initial feature extraction block where twice the input feature maps are extracted with half the image resolution achieved through convolutions with stride 2.

The extracted features are then passed through several hierarchical U-blocks HU (explained in the following) that down-sample the input feature maps, allowing efficient processing at a coarser scale before up-sampling the processed feature maps using subpixel convolutions.

To combine the outputs of the hierarchical U-blocks, a shared memory block (similar in construction to U-block but without the down-sampling and up-sampling operations) is used to process the extracted feature maps at different levels, then concatenating the memory block outputs before passing them to the final enhancement block.

In the final enhancement stage, 1×1 convolution is used to fuse the concatenated representations followed by up-scaling using sub-pixel convolution to generate the final complex output image.

Figure 6:
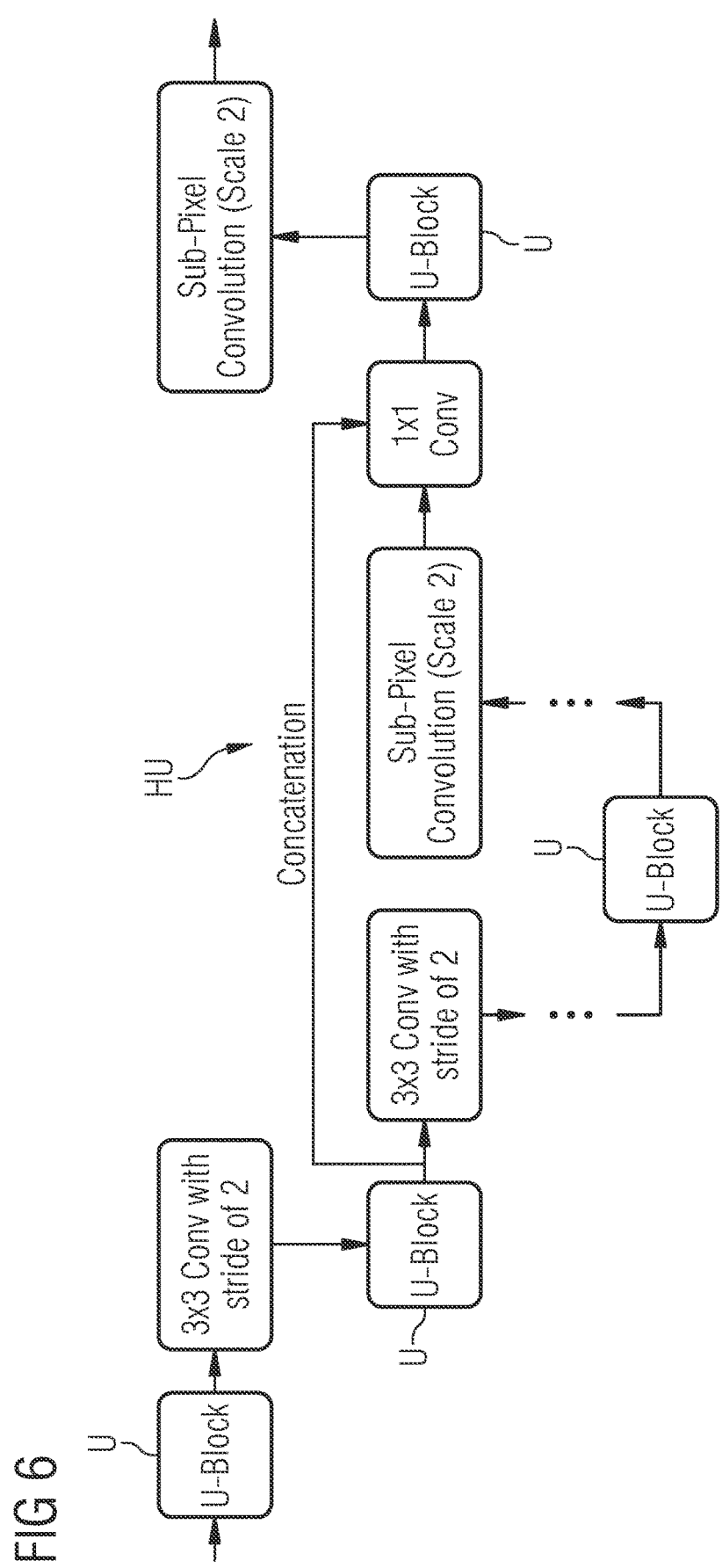
FIG. 6 shows one embodiment of a preferred architecture of a hierarchical U-block.

FIG. 6 shows a preferred architecture of a hierarchical U-block HU that is composed of a several U-blocks (explained in the following) that down-samples the input feature maps by convolutions with stride 2, allowing efficient processing at a coarser scale before up-sampling the processed feature maps using subpixel convolutions.

The example of the hierarchical U-block HU shows three layers, wherein the dotted lines of the lowest layer indicate that there may be more layers of a similar architecture of the upper two layers.

Here inputted data is processed by a U-block (shown in FIG. 7), then a 3×3 convolution occurs with a stride of 2. This happens several times before in the lowest layer a U-block processes the data that passes a sub-pixel convolution with the scale of 2 afterwards. After a 1×1 convolution, the U-block/sub-pixel convolution is performed several times until the upper layer is reached again.

Figure 7:
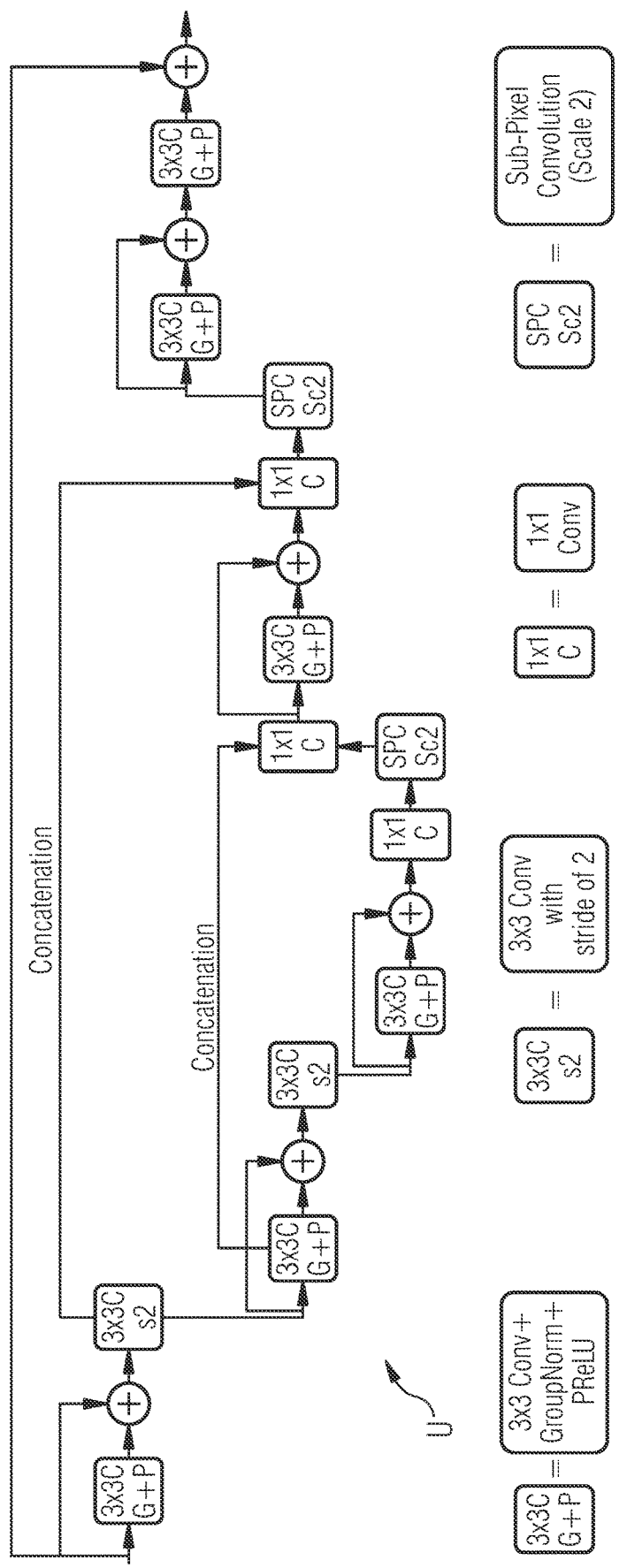
FIG. 7 shows one embodiment of a preferred architecture of a U-block.

FIG. 7 shows a preferred architecture of a U-block U used in the architecture of the hierarchical U-block HU. For a better overview, the sub-blocks of the U-block are symbols, with their meaning shown at the bottom of the figure. The first sub-block indicates a 3×3 convolution, a group normalization, and a function PReLu, each a well-known procedure in the art. The second sub-block indicates a 3×3 convolution with the stride of 2, also a well-known procedure in the art, as well as the third sub-block indicating a 1×1 convolution and the fourth sub-block indicating a sub-pixel convolution with the scale of 2.

The U-blocks design includes improved local and global residual connections to enhance information flow while maintaining efficient memory usage (compared to dense connections typically used).

Group normalization is adopted instead of typically used batch normalization layers to better deal with high-dimensional medical imaging data. Additionally, PReLU activation is used to provide the network with additional modeling flexibility.

Finally, while it is recommended to use sub-pixel convolutions for up-scaling the feature maps for computational efficiency, transposed convolutions with a scale of 2 can also be used to increase the model flexibility additionally.

Figure 8:
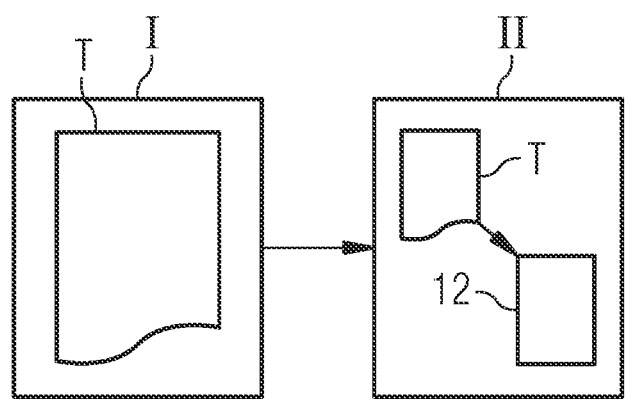
FIG. 8 shows a block diagram of the process flow of a preferred method according to one embodiment.

FIG. 8 shows a block diagram of the process flow of a preferred method for training a System 12 according to one embodiment.

In act I, a plurality of multi-coil training datasets T is provided, each training dataset T includes MRI-imaging data, especially under-sampled multi-coil k-space data, and a ground truth including fully-sampled multi-coil k-space data.

In act II, the system 12 is trained with the training datasets T concerning the ground truth of each training dataset T.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other acts or elements. The mention of a "unit" or a "device" does not preclude the use of more than one unit or device.

The invention claimed is:

1. A system for magnetic resonance imaging (MRI) coil sensitivity estimation, the system comprising:
a processor configured to estimate coil sensitivity with a network comprising: at least two cascades of regularization networks that are serially connected such that the output of one cascade is used as input of a following cascade, and at least two deepsets coil sensitivity map networks that are serially connected such that an output of one deepsets coil sensitivity map network is used as input of a following deepsets coil sensitivity map network,
wherein the outputs of the deepsets coil sensitivity map networks are also used as inputs for the cascades.

2. The system according to claim 1, wherein a first deepsets coil sensitivity map network of the serial connection is a deepsets coil sensitivity map estimation network and the following deepsets coil sensitivity map networks are deepsets coil sensitivity map refinement networks.

3. The system according to claim 1, wherein a number of the deepsets coil sensitivity map networks is equal to a number of the cascades.

4. The system according to claim 3, wherein each cascade is connected to an output of an individual deepsets coil sensitivity map network according to a serial arrangement of cascades and deepsets coil sensitivity map networks.

5. The system according to claim 1, wherein outputs of a number of the deepsets coil sensitivity map networks are weighted using shared weights.

6. The system according to claim 5, wherein all deepsets coil sensitivity map networks that are weighted using the shared weights are deepsets coil sensitivity map refinement networks.

7. The system according to claim 1, wherein one of the deepsets coil sensitivity map networks comprises a number of input channels each with a number of two or more successive deep iterative hierarchal networks (DIHN).

8. The system according to claim 7, wherein each channel has the same number of DIHN and the DIHN of the channels are united as a number of successive deep-sets-blocks, wherein each deep-sets-block comprises a DIHN for each channel followed by a RSS-normalization.

9. The system according to claim 7, wherein a deepsets coil sensitivity map estimation network comprises at an entrance of each channel a masking operator that zeros out all lines in k-space except for ACS lines, which is followed by an inverse Fourier transform to compute corresponding coil images.

10. The system according to claim 7, wherein at least one of the DIHNs has an architecture comprising a feature extraction block followed by two or more successive stages each comprising a hierarchical U-block and a shared memory block, wherein the data processed by one of the hierarchical U-blocks is sent to the memory block of this stage and the hierarchical U-block of the next stage, wherein the outputs of the memory blocks are weighted with shared weights and concatenated.

11. The system of claim 10, wherein the concatenated data is processed by a final enhancement stage comprising a 1×1 convolution followed by up-scaling using sub-pixel convolution.

12. The system according claim 10, wherein at least one of the hierarchical U-blocks has a U-net architecture using U-blocks, each being a U-net, with a contracting path and an expansive path, wherein the contracting path is a convolutional network that comprises a repeated application of a U-block followed by a convolution and the expansive path comprises up-convolutions and U-blocks.

13. The system according to claim 12, wherein the contracting path comprises a U-block followed by a 3×3 convolution, and/or the expansive path comprises a sub-pixel-convolution, and, between the contracting path and an expansive path, the data of the contracting path is further processed by an additional U-block.

14. The system according claim 10, wherein at least one of the hierarchical U-blocks is a U-block comprising a U-net or a series of such U-blocks.

15. The system according to claim 12, wherein at least one of the U-blocks has a U-net architecture with a contracting path and an expansive path, wherein the contracting path is a convolutional network that comprises a repeated application of convolutions, each followed by a rectified linear unit and a max pooling operation and the expansive path comprises up-convolutions.

16. The system according to claim 15, wherein the contracting path comprises a) a functional block comprising a convolution, a group normalization, and a rectified linear unit, and b) a functional block comprising a convolution, and/or the expansive path comprising a sub-pixel-convolution.

17. A method for training a reconstruction system, the method comprising the acts:
providing a plurality of multi-coil training datasets, each training dataset comprising MRI-imaging data, the MRI-imaging data comprising under-sampled multi-coil k-space data, and a ground truth comprising fully-sampled multi-coil k-space data, and
training of the reconstruction system with the training datasets concerning the ground truth of each training dataset, the reconstruction system comprising at least two cascades of regularization networks that are serially connected such that the output of one cascade is used as input of a following cascade, and at least two deepsets coil sensitivity map networks that are serially connected such that an output of one deepsets coil sensitivity map network is used as input of a following deepsets coil sensitivity map network, wherein the outputs of the deepsets coil sensitivity map networks are also used as inputs for the cascades.

18. A non-transitory computer-readable medium on which is stored instructions that can be read and executed by a processor for reconstruction, the non-transitory computer-readable medium comprising instructions for:
applying at least two cascades of regularization networks that are serially connected such that the output of one cascade is used as input of a following cascade, and
estimating coil sensitivity with at least two deepsets coil sensitivity map networks that are serially connected such that an output of one deepsets coil sensitivity map network is used as input of a following deepsets coil sensitivity map network, wherein the outputs of the deepsets coil sensitivity map networks are also used as inputs for the cascades.

\* \* \* \* \*